United States Patent
Wood et al.

(10) Patent No.: US 11,523,739 B2
(45) Date of Patent: *Dec. 13, 2022

(54) MULTISPECTRAL DETECTION AND PRESENTATION OF AN OBJECT'S CHARACTERISTICS

(71) Applicant: AccuVein Inc., Medford, NY (US)

(72) Inventors: Fred Wood, Medford, NY (US); Ron Goldman, Cold Spring Harbor, NY (US); Vincent Luciano, Shoreham, NY (US)

(73) Assignee: AccuVein, Inc., Medford, NY (US)

( * ) Notice: Subject to any disclaimer, the term of this patent is extended or adjusted under 35 U.S.C. 154(b) by 320 days.

This patent is subject to a terminal disclaimer.

(21) Appl. No.: 16/911,487

(22) Filed: Jun. 25, 2020

(65) Prior Publication Data

US 2020/0323432 A1 Oct. 15, 2020

Related U.S. Application Data (63) Continuation of application No. 14/053,775, filed on Oct. 15, 2013, now Pat. No. 11,051,697, which is a
(Continued)

(51) Int. Cl.
*A61B 5/00* (2006.01)
*A61M 5/42* (2006.01)
*A61B 90/00* (2016.01)

(52) U.S. Cl.
CPC .......... *A61B 5/0075* (2013.01); *A61B 5/0059* (2013.01); *A61B 5/0077* (2013.01);
(Continued)

(58) Field of Classification Search
CPC combination set(s) only.
See application file for complete search history.

(56) References Cited

U.S. PATENT DOCUMENTS 3,136,310 A 6/1964 Meltzer
3,349,762 A 10/1967 Kapany
(Continued)

FOREIGN PATENT DOCUMENTS

FR 2289149 5/1976
GB 1298707 12/1972
(Continued)

OTHER PUBLICATIONS

Wiklof, Chris, "Display Technology Spawns Laser Camera," LaserFocusWorld, Dec. 1, 2004, vol. 40, Issue 12, PennWell Corp., USA.
(Continued)

*Primary Examiner* — Joel F Brutus
(74) *Attorney, Agent, or Firm* — Thomas A. O'Rourke; Bodner & O'Rourke, LLP (57) ABSTRACT

An apparatus for capturing a multispectral image of an object is described. The apparatus includes one or more means for transmitting a beam of laser light at a first wavelength and a beam of laser light at one or more additional wavelengths different from the first wavelength. There is a means for causing the beams of laser light to travel in a coaxial path and a moving mirror. The beams of light bounce off the mirror thereby producing a two dimensional projection pattern. This pattern travels from the mirror along a first path to an object and wherein some of the laser light penetrates the object and travels to an internal structure of the object. The reflection of the laser light returns to a photo detector along a path different from said first path.

13 Claims, 10 Drawing Sheets

Related U.S. Application Data continuation of application No. 12/925,166, filed on Oct. 14, 2010, now Pat. No. 8,594,770, which is a continuation-in-part of application No. 11/478,322, filed on Jun. 29, 2006, now Pat. No. 8,478,386, and a continuation-in-part of application No. 11/700,729, filed on Jan. 31, 2007, now Pat. No. 8,838,210, and a continuation-in-part of application No. 11/807,359, filed on May 25, 2007, now Pat. No. 8,489,178, and a continuation-in-part of application No. 12/215,713, filed on Jun. 27, 2008, now Pat. No. 8,730,321, and a continuation-in-part of application No. 11/823,862, filed on Jun. 28, 2007, now Pat. No. 7,983,738.

(60) Provisional application No. 61/278,948, filed on Oct. 14, 2009.

(52) U.S. Cl.
CPC ............ *A61B 5/0088* (2013.01); *A61B 5/489* (2013.01); *A61B 5/4887* (2013.01); *A61B 2090/366* (2016.02); *A61M 5/427* (2013.01)

(56) References Cited

U.S. PATENT DOCUMENTS

| | | |
|---|---|---|
| 3,511,227 A | 5/1970 | Johnson |
| 3,527,932 A | 9/1970 | Thomas |
| 3,818,129 A | 6/1974 | Yamamoto |
| 3,984,629 A | 10/1976 | Gorog |
| 4,030,209 A | 6/1977 | Dreiding |
| 4,057,784 A | 11/1977 | Tafoya |
| 4,109,647 A | 8/1978 | Stern et al. |
| 4,162,405 A | 7/1979 | Chance et al. |
| 4,182,322 A | 1/1980 | Miller |
| 4,185,808 A | 1/1980 | Donohoe et al. |
| 4,213,678 A | 7/1980 | Pomerantzeff et al. |
| 4,265,227 A | 5/1981 | Ruge |
| 4,312,357 A | 1/1982 | Andersson et al. |
| 4,315,318 A | 2/1982 | Kato et al. |
| 4,321,930 A | 3/1982 | Jobsis et al. |
| 4,393,366 A | 7/1983 | Hill |
| 4,495,949 A | 1/1985 | Stoller |
| 4,502,075 A | 2/1985 | DeForest et al. |
| 4,510,938 A | 4/1985 | Jobsis et al. |
| 4,536,790 A | 8/1985 | Kruger et al. |
| 4,565,968 A | 1/1986 | Macovski |
| 4,567,896 A | 2/1986 | Barnea et al. |
| 4,576,175 A | 3/1986 | Epstein |
| 4,590,948 A | 3/1986 | Nilsson |
| 4,586,190 A | 4/1986 | Tsuji |
| 4,596,254 A | 6/1986 | Adrian et al. |
| 4,619,249 A | 10/1986 | Landry |
| 4,669,467 A | 6/1987 | Willett et al. |
| 4,697,147 A | 9/1987 | Moran et al. |
| 4,699,149 A | 10/1987 | Rice |
| 4,703,758 A | 11/1987 | Omura |
| 4,766,299 A | 8/1988 | Tierney et al. |
| 4,771,308 A | 9/1988 | Tejima et al. |
| 4,780,919 A | 11/1988 | Harrison |
| 4,799,103 A | 1/1989 | Muckerheide |
| 4,817,622 A | 4/1989 | Pennypacker et al. |
| 4,846,183 A | 7/1989 | Martin |
| 4,861,973 A | 8/1989 | Hellekson |
| 4,862,894 A | 9/1989 | Fujii |
| 4,899,756 A | 2/1990 | Sonek |
| 4,901,019 A | 2/1990 | Wedeen |
| 4,926,867 A | 5/1990 | Kanda et al. |
| RE33,234 E | 6/1990 | Landry |
| 4,938,205 A | 7/1990 | Nudelman |
| 5,074,642 A | 12/1991 | Hicks |
| 5,088,493 A | 2/1992 | Giannini et al. |
| 5,103,497 A | 4/1992 | Hicks |
| 5,146,923 A | 9/1992 | Dhawan |
| 5,174,298 A | 12/1992 | Dolfi et al. |
| 5,184,188 A | 2/1993 | Bull et al. |
| 5,214,458 A | 5/1993 | Kanai |
| 5,222,495 A | 6/1993 | Clarke et al. |
| 5,261,581 A | 11/1993 | Harden, Sr. |
| 5,293,873 A | 3/1994 | Fang |
| 5,339,817 A | 8/1994 | Nilsson |
| 5,371,347 A | 12/1994 | Plesko |
| 5,406,070 A | 4/1995 | Edgar et al. |
| 5,418,546 A | 5/1995 | Nakagakluchi et al. |
| 5,423,091 A | 6/1995 | Lange |
| 5,436,655 A | 7/1995 | Hiyama et al. |
| 5,445,157 A | 8/1995 | Adachi et al. |
| D362,910 S | 10/1995 | Creaghan |
| 5,485,530 A | 1/1996 | Lakowicz et al. |
| 5,487,740 A | 1/1996 | Sulek et al. |
| 5,494,032 A | 2/1996 | Robinson et al. |
| 5,497,769 A | 3/1996 | Gratton et al. |
| 5,504,316 A | 4/1996 | Bridgelall et al. |
| 5,519,208 A | 5/1996 | Esparza et al. |
| 5,541,820 A | 7/1996 | McLaughlin |
| 5,542,421 A | 8/1996 | Erdman |
| 5,598,842 A | 2/1997 | Ishihara et al. |
| 5,603,328 A | 2/1997 | Zucker et al. |
| 5,608,210 A | 3/1997 | Esparza et al. |
| 5,610,387 A | 3/1997 | Bard et al. |
| 5,625,458 A | 4/1997 | Alfano et al. |
| 5,631,976 A | 5/1997 | Bolle et al. |
| 5,655,530 A | 8/1997 | Messerschmidt |
| 5,678,555 A | 10/1997 | O'Connell |
| 5,716,796 A | 2/1998 | Bull et al. |
| 5,719,399 A | 2/1998 | Alfano et al. |
| 5,740,801 A | 4/1998 | Branson |
| 5,747,789 A | 5/1998 | Godik |
| 5,756,981 A | 5/1998 | Roustaei et al. |
| 5,758,650 A | 6/1998 | Miller et al. |
| 5,772,593 A | 6/1998 | Hakamata |
| 5,787,185 A | 7/1998 | Clayden |
| 5,814,040 A | 9/1998 | Nelson et al. |
| 5,836,877 A | 11/1998 | Zavisian |
| 5,847,394 A | 12/1998 | Alfano et al. |
| 5,860,967 A | 1/1999 | Zavislan et al. |
| 5,929,443 A | 7/1999 | Alfano et al. |
| 5,946,220 A | 8/1999 | Lemelson |
| 5,947,906 A | 9/1999 | Dawson, Jr. et al. |
| 5,966,204 A | 10/1999 | Abe |
| 5,966,230 A | 10/1999 | Swartz et al. |
| 5,969,754 A | 10/1999 | Zeman |
| 5,982,553 A | 11/1999 | Bloom et al. |
| 5,988,817 A | 11/1999 | Mizushima et al. |
| 5,995,856 A | 11/1999 | Mannheimer et al. |
| 5,995,866 A | 11/1999 | Lemelson |
| 6,006,126 A | 12/1999 | Cosman |
| 6,032,070 A | 2/2000 | Flock et al. |
| 6,056,692 A | 5/2000 | Schwartz |
| 6,061,583 A | 5/2000 | Ishihara et al. |
| 6,083,486 A | 7/2000 | Weissleder et al. |
| 6,101,036 A | 8/2000 | Bloom |
| 6,113,536 A | 9/2000 | Aboul-Hosn et al. |
| 6,122,042 A | 9/2000 | Wunderman et al. |
| 6,132,379 A | 10/2000 | Patacsil et al. |
| 6,135,599 A | 10/2000 | Fang |
| 6,141,985 A | 11/2000 | Cluzeau et al. |
| 6,142,650 A | 11/2000 | Brown et al. |
| 6,149,061 A | 11/2000 | Massieu et al. |
| 6,149,644 A | 11/2000 | Xie |
| 6,171,301 B1 | 1/2001 | Nelson et al. |
| 6,178,340 B1 | 1/2001 | Svetliza |
| 6,179,260 B1 | 1/2001 | Ohanian |
| 6,230,046 B1 | 5/2001 | Crane et al. |
| 6,240,309 B1 | 5/2001 | Yamashita et al. |
| 6,251,073 B1 | 6/2001 | Imran et al. |
| 6,263,227 B1 | 7/2001 | Boggett et al. |
| 6,272,376 B1 | 8/2001 | Marcu et al. |
| 6,301,375 B1 | 10/2001 | Choi |
| 6,305,804 B1 | 10/2001 | Rice et al. |
| 6,314,311 B1 | 11/2001 | Williams et al. |
| 6,334,850 B1 | 1/2002 | Amano et al. |
| 6,353,753 B1 | 3/2002 | Flock et al. |

(56) References Cited

U.S. PATENT DOCUMENTS

| | | |
|---|---|---|
| 6,424,858 B1 | 7/2002 | Williams |
| 6,436,655 B1 | 8/2002 | Bull et al. |
| 6,438,396 B1 | 8/2002 | Cook et al. |
| 6,463,309 B1 | 10/2002 | Ilia |
| 6,464,646 B1 | 10/2002 | Shalom et al. |
| 6,523,955 B1 | 2/2003 | Eberl et al. |
| 6,542,246 B1 | 4/2003 | Toida |
| 6,556,854 B1 | 4/2003 | Sato et al. |
| 6,556,858 B1 | 4/2003 | Zeman |
| 6,599,247 B1 | 7/2003 | Stetten |
| 6,631,286 B2 | 10/2003 | Pfeiffer et al. |
| 6,648,227 B2 | 11/2003 | Swartz et al. |
| 6,650,916 B2 | 11/2003 | Cook et al. |
| 6,689,075 B2 | 2/2004 | West |
| 6,690,964 B2 | 2/2004 | Bieger et al. |
| 6,702,749 B2 | 3/2004 | Paladini et al. |
| 6,719,257 B1 | 4/2004 | Greene et al. |
| 6,755,789 B2 | 6/2004 | Stringer et al. |
| 6,777,199 B2 | 8/2004 | Bull et al. |
| 6,782,161 B2 | 8/2004 | Barolet et al. |
| 6,845,190 B1 | 1/2005 | Smithwick et al. |
| 6,882,875 B1 | 4/2005 | Crowley |
| 6,889,075 B2 | 5/2005 | Marchitto et al. |
| 6,913,202 B2 | 7/2005 | Tsikos et al. |
| 6,923,762 B1 | 8/2005 | Creaghan, Jr. |
| 6,980,852 B2 | 12/2005 | Jersey-Willuhn et al. |
| 7,092,087 B2 | 8/2006 | Kumar et al. |
| 7,113,817 B1 | 9/2006 | Winchester, Jr. et al. |
| 7,158,660 B2 | 1/2007 | Gee, Jr. et al. |
| 7,158,859 B2 | 1/2007 | Wang et al. |
| 7,204,424 B2 | 4/2007 | Yavid et al. |
| 7,225,005 B2 | 5/2007 | Kaufman et al. |
| 7,227,611 B2 | 6/2007 | Hull et al. |
| 7,239,909 B2 | 7/2007 | Zeman |
| 7,247,832 B2 | 7/2007 | Webb |
| 7,280,860 B2 | 10/2007 | Ikeda et al. |
| 7,283,181 B2 | 10/2007 | Allen et al. |
| 7,302,174 B2 | 11/2007 | Tan et al. |
| 7,333,213 B2 | 2/2008 | Kempe |
| D566,283 S | 4/2008 | Brafford et al. |
| 7,359,531 B2 | 4/2008 | Endoh et al. |
| 7,376,456 B2 | 5/2008 | Marshik-Geurts et al. |
| 7,428,997 B2 | 9/2008 | Wiklof et al. |
| 7,431,695 B1 | 10/2008 | Creaghan |
| 7,448,995 B2 | 11/2008 | Wiklof et al. |
| 7,532,746 B2 | 5/2009 | Marcotte et al. |
| 7,545,837 B2 | 6/2009 | Oka |
| 7,559,895 B2 | 7/2009 | Stetten et al. |
| 7,579,592 B2 | 8/2009 | Kaushal |
| 7,608,057 B2 | 10/2009 | Woehr et al. |
| 7,699,776 B2 | 4/2010 | Walker et al. |
| 7,708,695 B2 | 5/2010 | Akkermans et al. |
| 7,792,334 B2 | 9/2010 | Cohen et al. |
| 7,846,103 B2 | 12/2010 | Cannon, Jr. et al. |
| 7,848,103 B2 | 12/2010 | Zhan |
| 7,904,138 B2 | 3/2011 | Goldman et al. |
| 7,904,139 B2 | 3/2011 | Chance |
| 7,925,332 B2 | 4/2011 | Crane et al. |
| 7,966,051 B2 | 6/2011 | Xie et al. |
| 8,032,205 B2 | 10/2011 | Mullani |
| 8,078,263 B2 | 12/2011 | Zeman et al. |
| 8,187,189 B2 | 5/2012 | Jung et al. |
| 8,199,189 B2 | 6/2012 | Kagenow et al. |
| 8,320,998 B2 | 11/2012 | Sato |
| 8,336,839 B2 | 12/2012 | Boccoleri et al. |
| 8,364,246 B2 | 1/2013 | Thierman |
| 8,467,855 B2 | 6/2013 | Yasui |
| 8,480,662 B2 | 7/2013 | Stolen et al. |
| 8,494,616 B2 | 7/2013 | Zeman |
| 8,498,694 B2 | 7/2013 | McGuire, Jr. et al. |
| 8,509,495 B2 | 8/2013 | Xu et al. |
| 8,537,203 B2 | 9/2013 | Seibel et al. |
| 8,548,572 B2 | 10/2013 | Crane |
| 8,630,465 B2 | 1/2014 | Wieringa et al. |
| 8,649,848 B2 | 2/2014 | Crane et al. |
| 2001/0006426 A1 | 7/2001 | Son et al. |
| 2001/0056237 A1 | 12/2001 | Cane et al. |
| 2002/0016533 A1 | 2/2002 | Marchitto et al. |
| 2002/0111546 A1 | 8/2002 | Cook |
| 2002/0118338 A1 | 8/2002 | Kohayakawa |
| 2002/0188203 A1 | 12/2002 | Smith et al. |
| 2003/0018271 A1 | 1/2003 | Kimble |
| 2003/0037375 A1 | 2/2003 | Riley et al. |
| 2003/0052105 A1 | 3/2003 | Nagano et al. |
| 2003/0120154 A1 | 6/2003 | Sauer et al. |
| 2003/0125629 A1 | 7/2003 | Ustuner |
| 2003/0156260 A1 | 8/2003 | Putilin et al. |
| 2004/0015062 A1 | 1/2004 | Ntziachristos et al. |
| 2004/0015158 A1 | 1/2004 | Chen et al. |
| 2004/0022421 A1 | 2/2004 | Endoh |
| 2004/0046031 A1 | 3/2004 | Knowles et al. |
| 2004/0171923 A1 | 9/2004 | Kalafut et al. |
| 2004/0222301 A1 | 11/2004 | Willins et al. |
| 2004/0237051 A1 | 11/2004 | Clauson |
| 2005/0017924 A1 | 1/2005 | Utt et al. |
| 2005/0033145 A1 | 2/2005 | Graham et al. |
| 2005/0043596 A1 | 2/2005 | Chance |
| 2005/0047134 A1 | 3/2005 | Mueller et al. |
| 2005/0085732 A1 | 4/2005 | Sevick-Muraca et al. |
| 2005/0085802 A1 | 4/2005 | Gruzdev et al. |
| 2005/0113650 A1 | 5/2005 | Pacione et al. |
| 2005/0131291 A1 | 6/2005 | Floyd et al. |
| 2005/0135102 A1 | 6/2005 | Gardiner et al. |
| 2005/0141069 A1 | 6/2005 | Wood et al. |
| 2005/0143662 A1 | 6/2005 | Marchitto et al. |
| 2005/0146765 A1 | 7/2005 | Turner et al. |
| 2005/0154303 A1 | 7/2005 | Walker et al. |
| 2005/0157939 A1 | 7/2005 | Arsenault et al. |
| 2005/0161051 A1 | 7/2005 | Pankratov et al. |
| 2005/0168980 A1 | 8/2005 | Dryden et al. |
| 2005/0174777 A1 | 8/2005 | Cooper et al. |
| 2005/0175048 A1 | 8/2005 | Stern et al. |
| 2005/0187477 A1 | 8/2005 | Serov et al. |
| 2005/0215875 A1 | 9/2005 | Khou |
| 2005/0265586 A1 | 12/2005 | Rowe et al. |
| 2005/0281445 A1 | 12/2005 | Marcotte et al. |
| 2006/0007134 A1 | 1/2006 | Ting |
| 2006/0020212 A1 | 1/2006 | Xu et al. |
| 2006/0025679 A1 | 2/2006 | Viswanathan et al. |
| 2006/0052690 A1 | 3/2006 | Sirohey et al. |
| 2006/0081252 A1 | 4/2006 | Wood |
| 2006/0100523 A1 | 5/2006 | Ogle et al. |
| 2006/0103811 A1 | 5/2006 | May et al. |
| 2006/0122515 A1 | 6/2006 | Zeman et al. |
| 2006/0129037 A1 | 6/2006 | Kaufman et al. |
| 2006/0129038 A1 | 6/2006 | Zelenchuk et al. |
| 2006/0151449 A1 | 7/2006 | Warner, Jr. et al. |
| 2006/0173351 A1 | 8/2006 | Marcotte et al. |
| 2006/0184040 A1 | 8/2006 | Keller et al. |
| 2006/0206027 A1 | 9/2006 | Malone |
| 2006/0232660 A1 | 10/2006 | Nakajima et al. |
| 2006/0253010 A1 | 11/2006 | Brady et al. |
| 2006/0271028 A1 | 11/2006 | Altshuler et al. |
| 2006/0276712 A1 | 12/2006 | Stothers |
| 2007/0015980 A1 | 1/2007 | Numada et al. |
| 2007/0016079 A1 | 1/2007 | Freeman et al. |
| 2007/0070302 A1 | 3/2007 | Govorkov et al. |
| 2007/0115435 A1 | 5/2007 | Rosendaal |
| 2007/0129634 A1 | 6/2007 | Hickey et al. |
| 2007/0176851 A1 | 8/2007 | Willey et al. |
| 2007/0238957 A1 | 10/2007 | Yared |
| 2008/0045841 A1 | 2/2008 | Wood et al. |
| 2008/0147147 A1 | 6/2008 | Griffiths et al. |
| 2008/0194930 A1 | 8/2008 | Harris et al. |
| 2008/0214940 A1 | 9/2008 | Benaron |
| 2009/0018414 A1 | 1/2009 | Toofan |
| 2009/0082629 A1 | 3/2009 | Dotan |
| 2009/0171205 A1 | 7/2009 | Kharin et al. |
| 2010/0051808 A1 | 3/2010 | Zeman et al. |
| 2010/0061598 A1 | 3/2010 | Seo |
| 2010/0087787 A1 | 4/2010 | Woehr et al. |
| 2010/0177184 A1 | 7/2010 | Berryhill et al. |
| 2010/0312120 A1 | 12/2010 | Meier |
| 2011/0275932 A1 | 11/2011 | Leblond et al. |

(56) References Cited

U.S. PATENT DOCUMENTS

| | | |
|---|---|---|
| 2013/0147916 A1 | 8/2013 | Bennett et al. |
| 2014/0039309 A1 | 2/2014 | Harris et al. |
| 2014/0046291 A1 | 2/2014 | Harris et al. |
| 2014/0194747 A1 | 7/2014 | Kruglick |

FOREIGN PATENT DOCUMENTS

| | | |
|---|---|---|
| GB | 1507329 | 4/1978 |
| JP | S60-108043 A | 6/1985 |
| JP | 04-042944 | 2/1992 |
| JP | 07-255847 | 10/1995 |
| JP | 08-023501 A | 1/1996 |
| JP | 08-164123 | 6/1996 |
| JP | 2000-316866 A | 11/2000 |
| JP | 2002-328428 A | 11/2002 |
| JP | 2002-345953 A | 12/2002 |
| JP | 2004-237051 | 8/2004 |
| JP | 2004-329786 A | 11/2004 |
| JP | 2006-102360 | 4/2006 |
| KR | 2003-0020152 A | 3/2003 |
| WO | WO 1994 22370 | 10/1994 |
| WO | WO 1996 39925 | 12/1996 |
| WO | WO 1998 26583 | 6/1998 |
| WO | WO 1999 48420 | 9/1999 |
| WO | WO 2001-82786 | 11/2001 |
| WO | WO 2003-009750 | 2/2003 |
| WO | WO 2005-053773 | 6/2005 |
| WO | WO 2007-078447 | 7/2007 |

OTHER PUBLICATIONS

Nikbin, Darius, "IPMS Targets Colour Laser Projectors," Optics & Laser Europe, Mar. 1006, Isue 137, p. 11.
http://sciencegeekgirl.wordpress.com/category/science-myths/page/2/Myth 7: Blood is Blue.
http://www.exptoratorium.edu/sports/hnds_up/hands6.html "Hands Up! To Do & Notice: Getting the Feel of Your Hand".
http://www.wikihow.com/See-Blook-Veins-in-Your-Hand-With-a-Flashlight "How to See Blood Veins in Your Hand With a Flashlight".

MULTISPECTRAL DETECTION AND PRESENTATION OF AN OBJECT'S CHARACTERISTICS

CROSS-REFERENCE TO RELATED APPLICATIONS

This application is a continuation of U.S. patent application Ser. No. 14/053,775, filed on Oct. 15, 2013, which is a continuation of U.S. patent application Ser. No. 12/925,166, filed on Oct. 14, 2010, now issued as U.S. Pat. No. 8,594,770, which claims priority on Provisional Patent Application Ser. No. 61/278,948, filed Oct. 14, 2009, and which is a continuation-in-part of: application Ser. No. 11/478,322, filed on Jun. 29, 2006, now issued as U.S. Pat. No. 8,478,386; U.S. patent application Ser. No. 11/700,729, filed Jan. 31, 2007; U.S. patent application Ser. No. 11/807,359, filed May 25, 2007, now issued as U.S. Pat. No. 8,489,178; U.S. patent application Ser. No. 12/215,713, filed Jun. 27, 2008; and U.S. patent application Ser. No. 11/823,862, filed Jun. 28, 2007, now issued as U.S. Pat. No. 7,983,738. All of the foregoing disclosures are hereby incorporated by reference.

FIELD OF THE INVENTION

The present invention relates to improvements in multi-spectral imaging for determining the characteristics of an objects, and more particularly to improvements which are capable of providing imaging of internal structure through trans-illumination apparatus and techniques.

BACKGROUND OF THE INVENTION

The human visual system is able to detect light in a range of wavelengths that are typically described as "visible light." The longest wavelengths detected are red, the mid range is green and shortest wavelengths are blue. Long wavelength light such as infrared and short wavelength light such as ultraviolet are invisible to the human eye. The characteristics of an object that we can determine with the unaided eye are limited to those that can be detected in this spectrum. Furthermore, the trichromatic system used by the eye is broadband in nature and cannot see narrowband artifacts such as would be seen by a spectrophotometer.

Several products have reached market that emit infrared light on an object and use the reflected light to detect a pattern of varying contrast in the infrared spectrum. The device then projects an image that follows those contrast changes using a wavelength within the visible spectrum. In one such product, the AccuVein AV300, detects a pattern of absorption and reflection in the infrared and re-projects that pattern as red. Given that hemoglobin absorbs infrared light to a greater degree than the surrounding tissue, the projected pattern can be used by a medical practitioner to identify the position of a vein to be used for venipuncture.

In other products, the light is captured and the processed image is displayed on a remote screen such as an LCD panel or through an eyepiece that is in line with the object.

These contrast enhancement products act as color shifters. Just as the human eye would detect variations in absorption and reflection in the three colors it can see (red, green and blue), these contrast enhancers detect the variations at wavelengths outside the visible spectrum and display the corresponding pattern inside the visible spectrum.

OBJECTS OF THE INVENTION

1. It is an object of the invention to use a laser camera to detect characteristics of an observed object based on the reflection and absorption of the laser light or based on the re-emission of absorbed light at a different wavelength than the incident light.
2. It is an object of the invention to use a single or multiple wavelengths of laser light to detect characteristics of an observed object based on the reflection and absorption of the laser light based or the re-emission of absorbed light at a different wavelength than the incident light.
3. It is an object of the invention to use multi-spectral imaging by capturing light from wavelengths beyond just the visible light range, such as infrared and UV. This allows extraction of additional information that the human eye fails to capture with its receptors for red, green and blue.
4. It is an object of the invention to use hyper-spectral imaging by capturing information from a plurality of wavelengths including and beyond the visible light range, such as infrared and UV. This allows extraction of additional information that the human eye fails to capture with its broadband receptors.
5. It is an object of the invention to detect characteristics of the observed object both of the surface of the observed object when it its opaque and of the surface and below the surface when the object is translucent.
6. It is an object of the invention to improve the quality of detection of characteristics of the observed object by iteratively varying in real time the intensity of the light emitted by the laser camera based on the previously detected characteristics of the observed object.
7. It is an object of the invention to present detected characteristics of the observed object back on to the object itself or on to a display visible to the user of the device or both using contrast, color, false color, icons or text or a combination of these modalities.
8. It is an object of the invention to capture detected characteristics of the observed object for the purpose of record keeping or for the purpose of post processing or for the purposes of detecting changes and trends in the observed object or a combination of these purposes.
9. It is an object of the invention to combine the detected characteristics of the observed object with external sources of data for the purposes of refining and/or extending the meaning of the detected characteristics.
10. It is an object of the invention to improve the detection characteristics of the system by using transillumination.
11. It is an of the invention to detect characteristics of many types of objects and materials including veins, arteries, teeth, metals and plastics.

BRIEF SUMMARY OF THE INVENTION

The invention disclosed herein extends this concepts described in the parent applications in several novel ways, which can be used individually, or in combination.

1. By using more than one wavelength of light for analysis, additional characteristics about the object being scanned can be determined and then this additional information can be re-projected back on to the surface within the visible spectrum making these characteristics visible to a human either as a color-shifted image or as a false-color image. In this embodiment the device acts like a photo spectrometer that re-projects a visible image back on the object.
2. Contrast enhancement products rely on differential absorption and reflection of light (i.e. they detect contrast changes) and then re-project that contrast pattern. An alternative embodiment can also use florescence of the object being scanned by shining light of one wavelength on to the object and detecting light at another wavelength returned from the object and then this information being re-projected back on to the surface within the visible spectrum making these characteristics visible. In this embodiment the device acts like a spectroscope that re-projects a visible image back on the object.
3. This invention can further use florescence or color change of a material applied to the object being scanned that based on the characteristics of the object exhibits either a color change (and can therefore use contrast enhancement) or a florescence at one or more wavelengths of incident light.

The invention can be further enhanced by combining some or all of these techniques to detect and project different characteristics of the object being scanned and projecting them back on the object.

While many of the descriptions are for embodiments that use re-projection back on to the object under study as the user interface, embodiments with user interfaces remote from the object such as an LCD screen will be useful in many applications. Furthermore, the combination of re-projection and remote displays will also be useful in many applications.

While the devices and systems described herein focus on multispectral systems and describe specific embodiments of said devices and systems, the methods, features, functions, abilities, and accessories described in the parent applications apply fully.

DETAILED DESCRIPTION OF THE INVENTION

As is well known in the art, a laser camera works by emitting one or more laser beams and moving those beams in a pattern such that the beams cross over the area of an object of which an image is to be captured. A photo detector element in the camera captures the changes in light reflected from the object and uses that light change to create an image of the observed object. Note that as with a traditional camera, "object" should be read in this explanation as an object or as a group of objects (e.g., an apple or a still life that includes an apple). The pattern in which the beam is moved is unimportant as long as the position at which it strikes the object can be determined either directly or inferentially. Examples of patterns that can be used include raster and lissajous.

Figure 1:
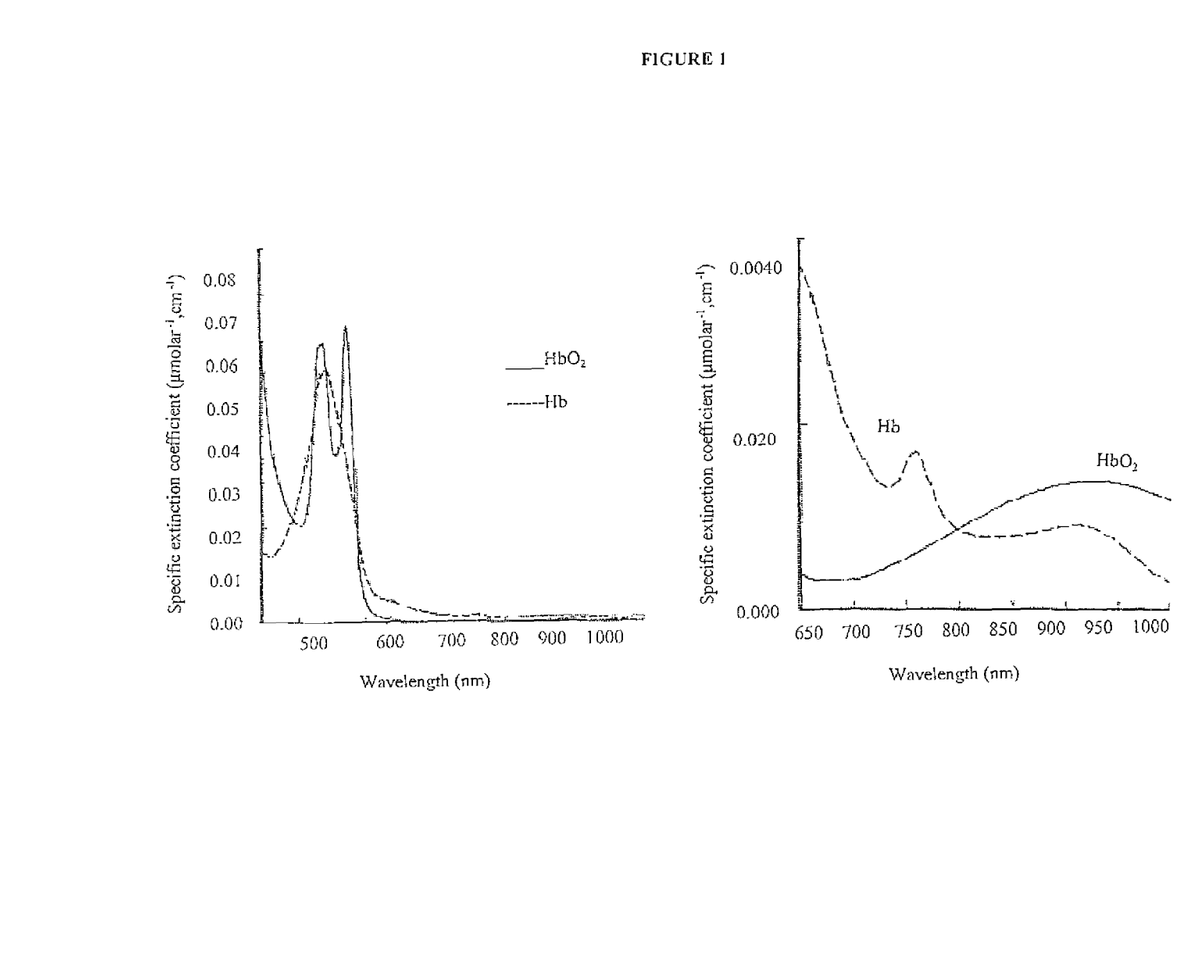
FIG. 1 shows the different absorption spectrum for human deoxygenated hemoglobin, and for oxygenated hemoglobin.

As previously mentioned, the AccuVein AV300 is a laser camera system that uses a single infrared laser scanned over the object (in this case the human body) to determine the position of hemoglobin as a proxy for the position of a vein. The device uses the general characteristic of hemoglobin in that it absorbs infrared light to a greater degree than surrounding tissue. As seen in FIG. 1, there is a slightly different absorption spectrum for deoxygenated hemoglobin (as would be found in veins) and oxygenated hemoglobin (as would be found in arteries).

Through the addition of a second infrared laser of a different wavelength, or through the addition of a tunable laser allowing the wavelength to be changed, the invention could detect the difference between a vein and an artery. The user interface could then use one or more of several techniques to indicate the type of hemoglobin detected.

While a range of techniques could be used for the detection algorithm, in one embodiment the following truth table could be used:
1. Less reflection seen in either wavelength when compared to surrounding tissue? Position contains hemoglobin
2. Wavelength one reflection<wavelength two reflection? Position contains oxygenated hemoglobin
3. Wavelength one reflection>wavelength two reflection? Position contains deoxygenated hemoglobin Furthermore, a range of techniques could be used for the user interface. These include:
1. Project an image back on to the object that is scanned using a visible wavelength laser showing contrast changes between "hit" areas and surrounding areas
2. Project said areas using continuously variable brightness to track the contrast changes.
3. Project said areas using enhanced contrast to highlight the position of the detected hemoglobin
4. Project said areas using a color map (sometimes known as false color) where different colors represent different characteristics.

While the use of infrared wavelengths to detect different types of hemoglobin are used for this illustrative example, there are many characteristics well know in the art that can be determined by the absorption spectrum of an object that the invention would be equally suited to.

One embodiment of the invention uses a one or more data capture techniques as discussed previously and provides user feedback by re-projecting a re-colored image back on to the area being scanned. Since it is possible for one or more of the wavelengths of light being captured to overlap with the wavelengths of light being projected it is necessary to implement one or more techniques to prevent the projected light from being confused with the detected light.

These techniques include the following and can be combined:
1. Detect for a short period (e.g., a pixel time) and project for a short period.
2. Detect for a scan line and project for a scan line.
3. Detect for multiple scan lines and project for a scan line.
4. Detect for a scan line and repeat project for multiple scan lines.
5. Detect for a frame and project for a frame The illustrative uses of asymmetrical detection and projection allows a balance between the amount of time that might be needed for capture and the processing the captured information and the need to have a sufficiently high projection rate to provide a good user experience. Other asymmetrical combinations are possible.

An alternative embodiment of the invention is one in which diffuse light of one or more wavelengths is emitted and then reflected by the object under study. A digital camera using technology such as CMOS or CCD sensors captures an image of five object being studied to determine the reflection/absorption spectrum of the object. By controlling the emitted light wavelengths or by modifying the sensitivity spectrum of the image sensor, the spectral characteristics of the object can be determined.

Examples of modifying the response characteristics of the image sensor have been seen in the literature. For example, in "Laser Focus World" there is a discussion in an article titled "CMOS imager with mosaic filter detects skin disorders". Another related discussion is found in another article with the title "MEDICAL IMAGING: Real-time multispectral imager promises portable-diagnosis."

Transillumination

Figure 2:
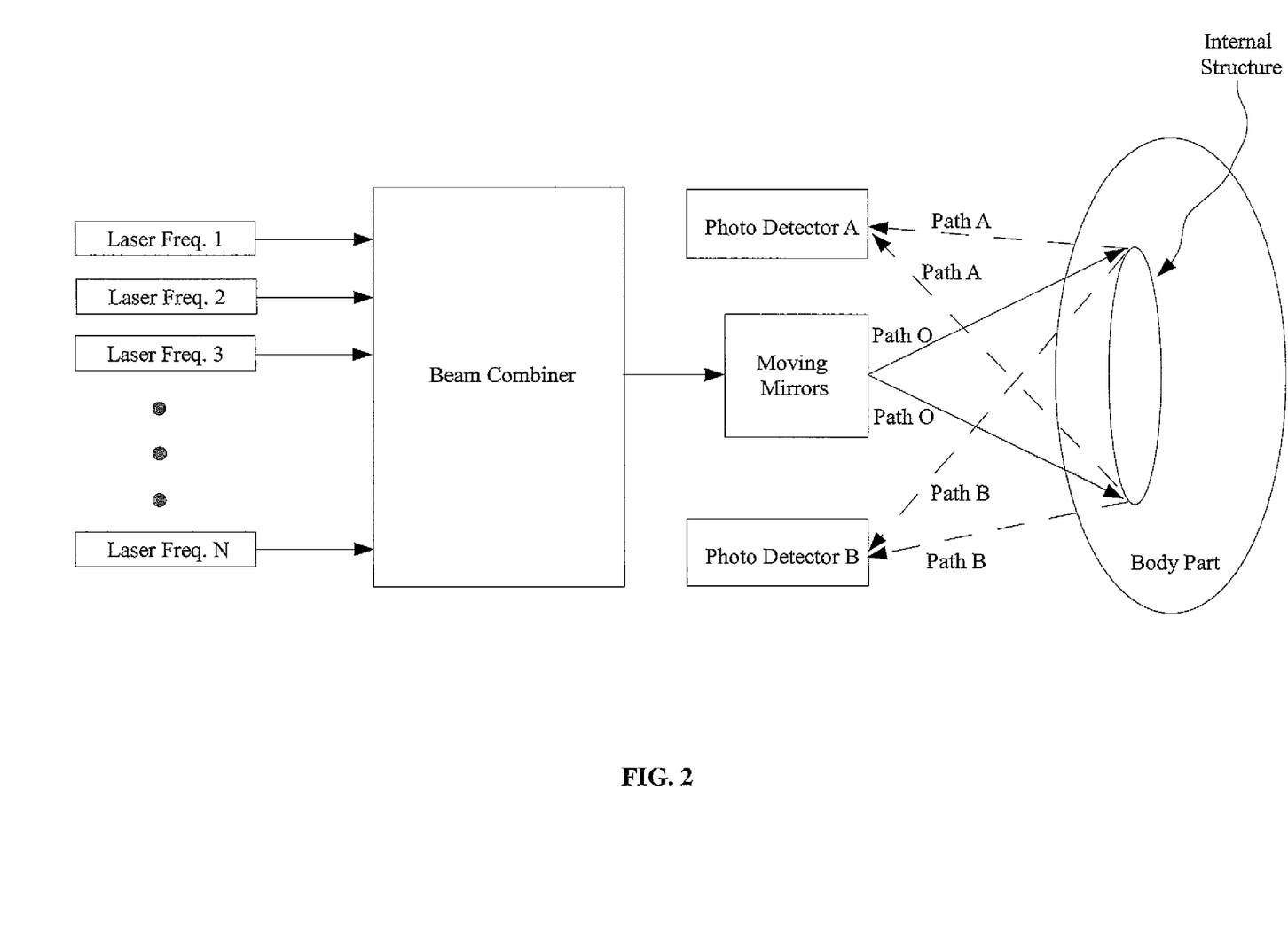
FIG. 2 shows a laser camera system having multiple frequency lasers for multispectral imaging applications.

FIG. 2 shows a laser camera having multiple frequency lasers for multispectral imaging applications. Multiple lasers (Laser Freq 1-Laser Freq N) are combined so that they are exiting coaxially from the Beam Combiner. They then bounce off a biaxial moving mirror (or a separate X and Y mirror) to produce a two-dimensional projection pattern. The pattern travels along Path O to a Body Part. Some of the Laser Freq wavelengths penetrate the Body Part and travel to the Internal Structure. The various Laser Freq wavelengths each interact with the internal structure in differing ways (varying levels of absorption and reflections). The reflections of the Laser Frequencies 1-N return to Photo Detector A and Photo Detector B along Path A and Path B respectively. The Photo Detectors may be, for example, a photo diode.

In one mode of operation, each Laser Freq 1-N is sequentially turned on for one frame of projection. The reflected light received at Photo Detectors A+B for that frame is then stored in a first frame memory location (not shown). In this manner, by sequentially stepping through Freq 1-N a multispectral image is stored in sequential frames of memory locations 1-N.

A characteristic of the system shown in FIG. 2 is that some portion of the projected Laser Freqs 1-N are reflected off the surface of the Body Part back to the Photo Detectors A+B. In the case where you are only interested in the characteristics of the Internal Structure, the reflections off the surface of the Body Part are essentially "noise" to the system. External structures, such a hair, scars curvature of the body part, differences in reflectivity of exterior regions of the Body Part, all have the effect of generating noise that detract from imaging the Internal Structure. Algorithms can be written to help distinguish between the Internal Structure and the "noise", however, such algorithms are rarely perfect.

One method of penetrating deeper into the Body Part to see deeper Internal Structures is to increase the power output of the Lasers 1-N. However, as laser power is increased, the reflections off the external surface of the Body Part also increases. Eventually the Photo Detectors A+B, and the associated circuitry after them (not shown), gets saturated and the details of the Internal Structure get washed away.

Figure 3A:
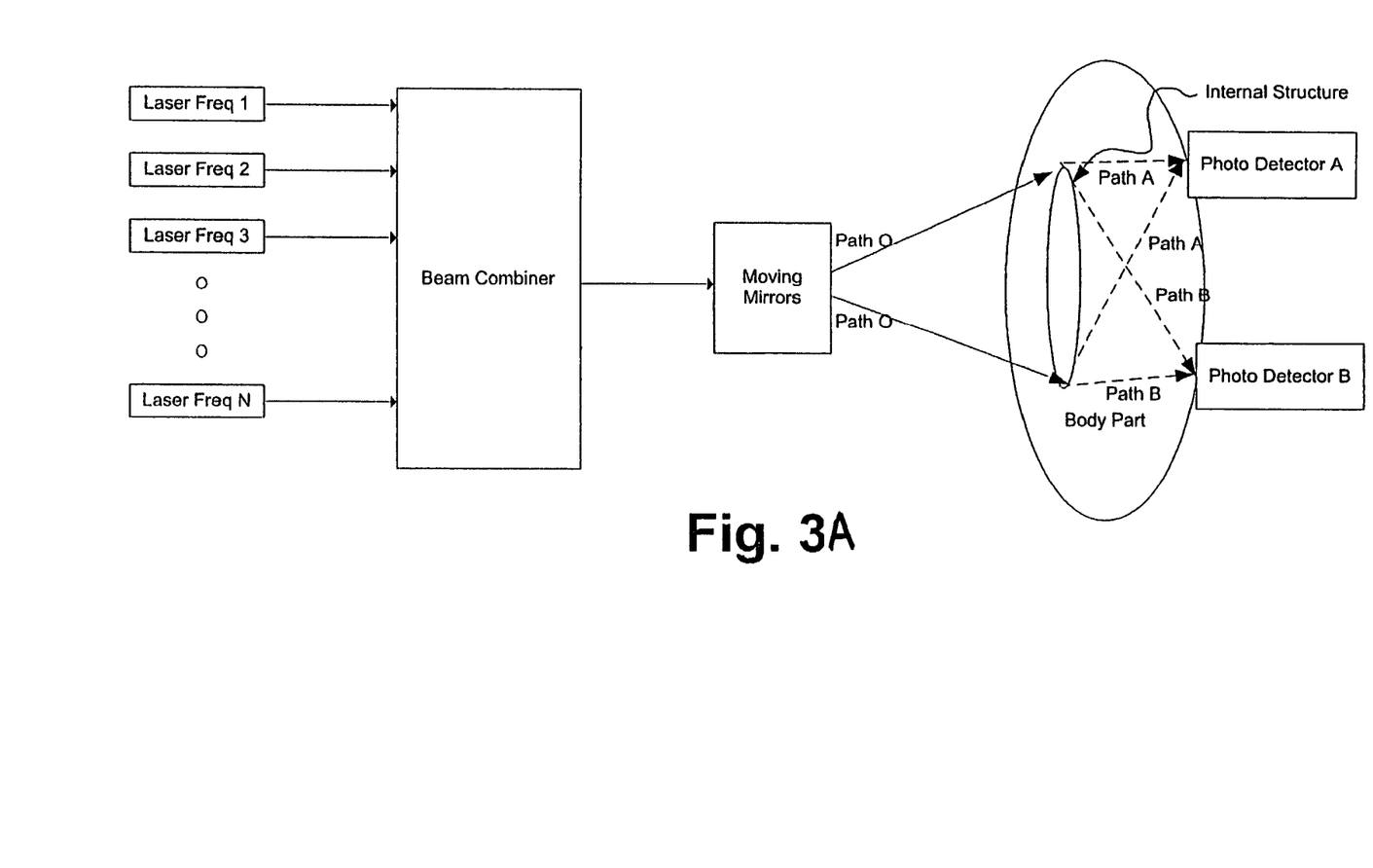
FIG. 3A shows the laser camera system of FIG. 2, but with a pair of photo detectors positioned to avoid laser light reflected from the skin surface, and positioned for trans-illumination of an internal structure.

FIG. 3A shows a system similar to that of FIG. 2 except that the Photo Detectors A and B are moved and are placed in a way that no light from lasers 1-N reflected from the surface of the skin can reach them. For example, they may be physically touching the skin of the Body Part (FIG. 3A). This type of system will be referred hereinafter as a transillumination laser system, wherein the Laser 1-N, upon hitting the Internal Structure, is then carried internal to the Body Part, with some portion of the light (shown as Path A and Path B) eventually hitting the Photo Detector A and/or B which are placed against the skin of the Body Part. Accordingly, the Laser Light that reaches Photo Detector A and/or B vary as a function of the Internal Structure's absorption and reflection of the Laser Light. For example, the presence of a highly absorptive tissue in the light path would decrease the signal generated by the Photo Detectors, while the presence of a highly scattering tissue would increase it. It should be noted that the position of the Photo Detectors does not need to be on the side opposite the output laser Path O. The Photo Detectors can be placed anywhere on the Body Part, as long as sufficient internally carried light manages to reach the Photo Detectors.

Figure 3B:
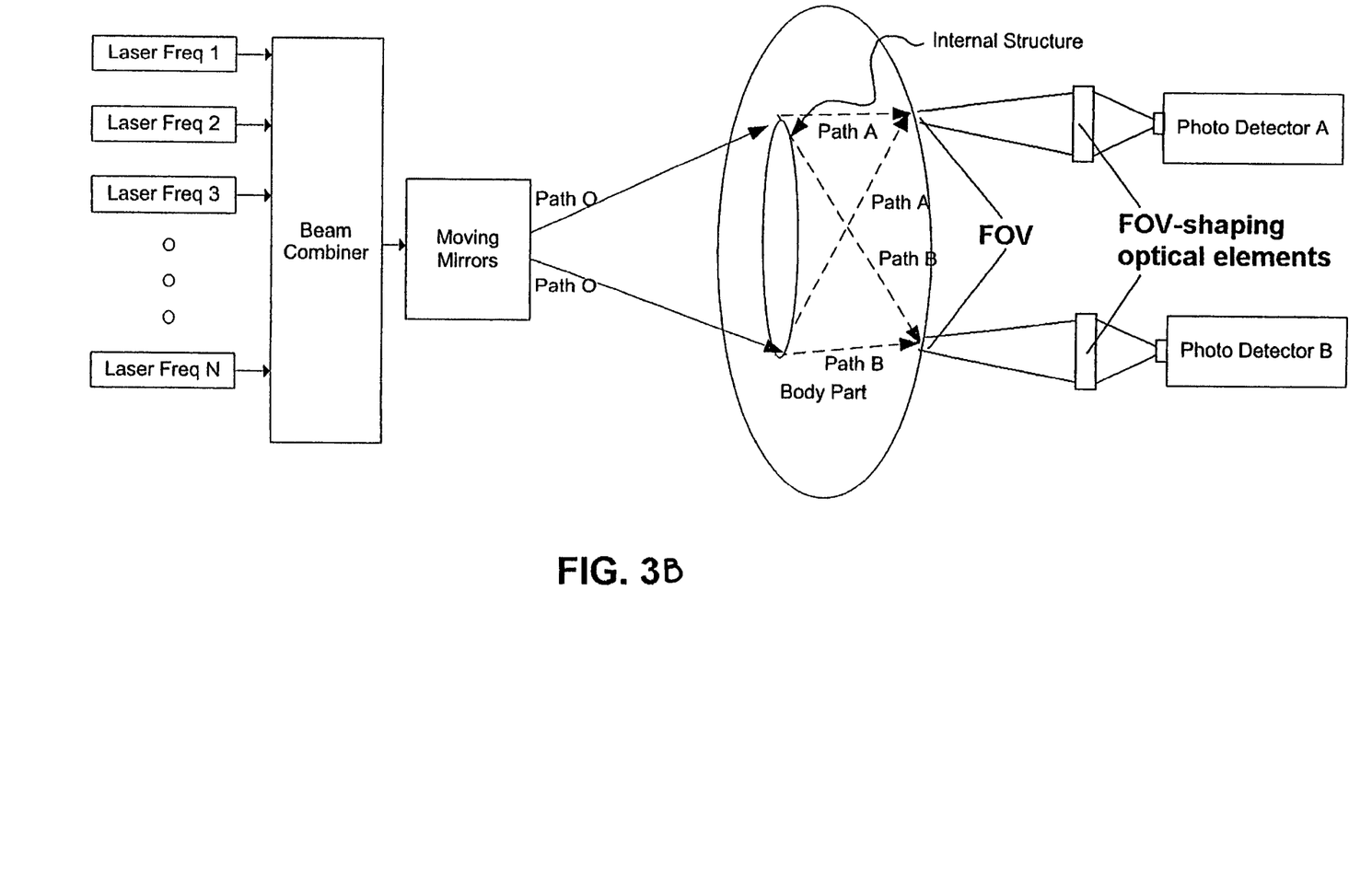
FIG. 3B shows the laser camera system of FIG. 3, but where the photo detectors are configured to have their field-of-view restricted by optical elements, to areas of the skin of the body part that are not directly illuminated by the laser light.

Nor do the Photo Detectors have to be physically touching the skin of the Body Part. Instead, they may configured to have their Field-of-View (FOV) restricted to areas of the skin the Body Part which are not directly illuminated by lasers 1-N (FIG. 3b). The FOV may be shaped by lenses, Fresnel lenses, curved mirrors or other optical elements. Additionally, the FOV of the Photo Detectors does not have to be stationary. Instead, it can be moving synchronously with the scanning system in such manner that no light from lasers 1-N reflected from the surface of the skin can reach them.

In the transillumination laser system of FIG. 3A/FIG. 3B, as the intensity of the Laser 1-N is increased, none of reflections off the surface of the Body Part are projected onto Photo Detector A or B. Accordingly, the power of Laser 1-N can be significantly increased to allow for imaging of deeper Internal Structures without concern for saturation due to reflections off the surface of the Body Part. Further, surface artifacts such as hair and surface blemishes are largely ignored. Essentially, the transillumination system allows for a greater signal to noise separation between the internal structure (the signal) and the reflections occurring off the surface of the Body Part (the noise). This allows for a much higher contrast ratio image of the underlying Internal Structure. In both FIGS. 2 and 3A/3B individual Laser Freq 1-N were shown as individual blocks. It is also possible to purchase a tunable laser that can output a wide range of laser frequencies. This eliminates the need for the Beam Combiner of FIGS. 2 and 3A/3B. OpoTek Inc. sells a tunable laser system called the VIBRANT (HE) 355 II which can output frequencies in the range of 410-2400 nm. In such a case, the tunable laser will be set to a desired frequency for a single frame and the appropriate image captured. The tunable laser is set to the next frequency and its corresponding image is captured. This cycle repeats until all laser frequencies are cycled. This allows for a very large number of frequencies to be utilized.

Alternatively, a wide-band laser, which emits light different wavelength simultaneously, may be used. Such lasers are known to be constructed with active media been confined to an optical fiber with various doping elements with overlapping emission spectra. Alternatively, the pulsed lasers with ultra-short pulses may be used where the spectrum is broadened by the sidebands of the frequencies associated with the pulse duration. One example of such lasers is a mode-locked laser.

Figure 9A:
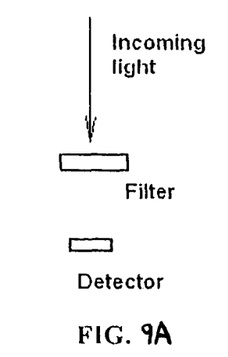
FIG. 9A shows a color filter which limits the response of the photo detector.
Figure 9B:
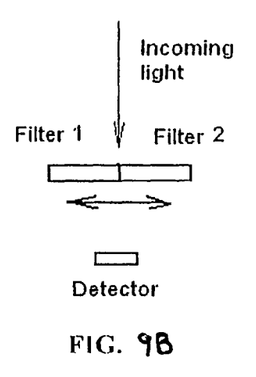
FIG. 9B shows a first filter and a second filter being used to limit the response of the photo detector.
Figure 9C:
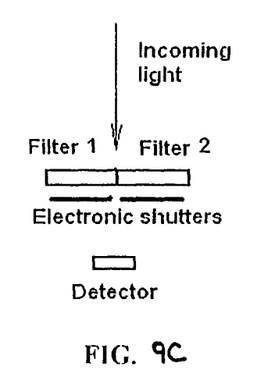
FIG. 9C shows the first and second filters of FIG. 9B with a pair of electronic shutters also being used to electro-optically limit the response of the photo detector.
Figure 9D:
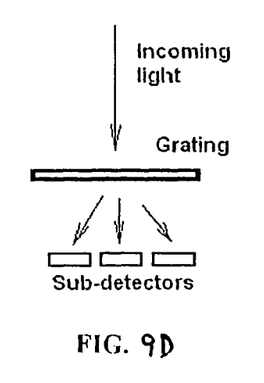
FIG. 9D shows a grating being used to transmit light to three different color-resolved detectors.

In this case, different wavelengths will be detected by Photo Detectors with different spectral responses. In one embodiment, identical Photo Detectors with broadband response may have color filters which limit the response of each Detector to a narrow band of wavelengths (FIG. 9). Alternatively, the filters may be applied selectively, by moving or masking parts of the filter either mechanically (FIG. 9b). or electro-optically (FIG. 9c), using electronically-controlled optical elements such as LCD shutters. Yet alternatively, color-resolved Detectors may be used, where the light of different wavelength is directed toward different detector elements by a grating or other suitable optical element (FIG. 9d).

Figure 4:
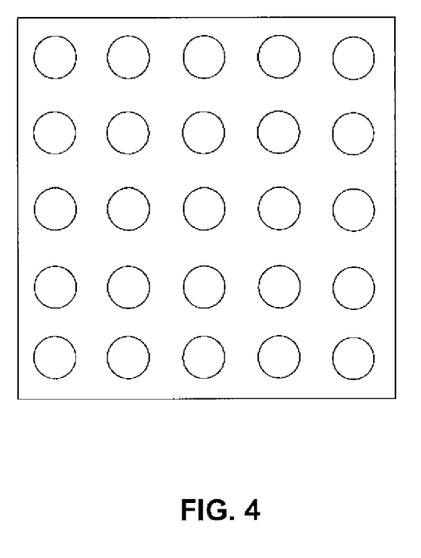
FIG. 4 shows a 5×5 array of photo detectors.

In a transillumination laser system, single, multiple, or arrays of Photo Detectors may be used instead of the two Photo Detectors shown in FIG. 3A/FIG. 3B. FIG. 4 shows a 5 by 5 array of Photo Detectors. This array of Photo Detectors is then placed in contact with the Body Part to receive the internally reflected Laser 1-N. In this embodiment the array can be placed anywhere on the Body Part except along optical Path O of FIG. 3A/FIG. 3B. A large array of Photo Detectors increases the photo detection area, thereby capturing more of the internally reflected light. Further, the Photo Detector array can uniformly distribute the receiving Photo Detectors over area so that it more uniformly receives the internally reflected light. In this manner, "hot spots" associated with fewer Photo Detectors can be minimized.

Figure 5:
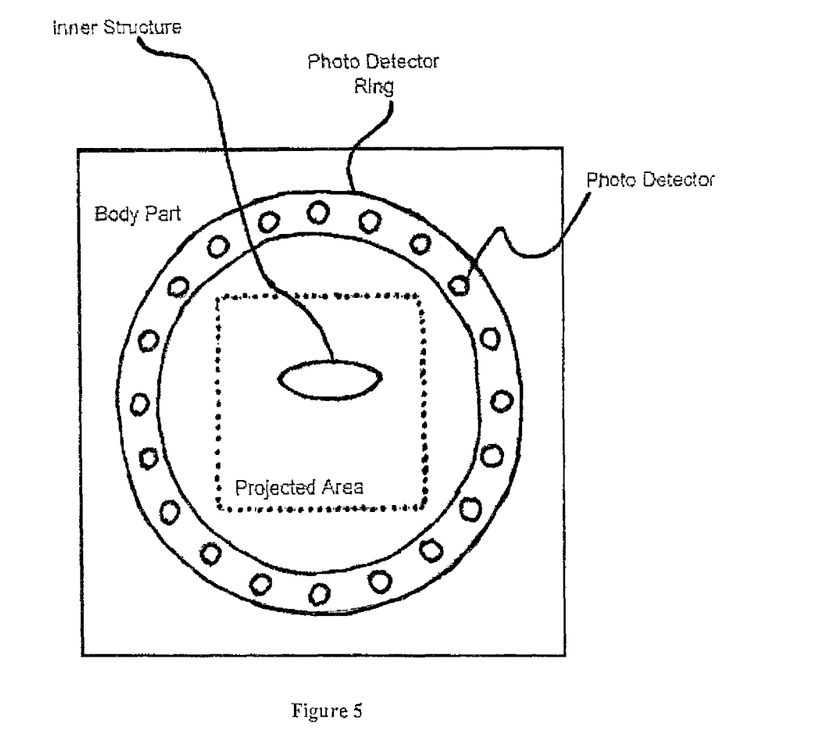
FIG. 5 shows a photo detector ring with a circular array of photo detectors arranged around the body part to be penetrated to detect laser light scattered from an inner structure.

FIG. 5 shows an embodiment wherein a Photo Detector Ring is placed around the Projected Area of the Laser 1-N. More specifically, it is a view from the perspective of the mirrors of FIG. 3. In this embodiment, the ring is placed against the surface of the Body Part in a position such that the Laser 1-N projected along Path O in 3A/FIG. 3B fails inside the inner edge of the Ring. The Lasers 1-N penetrates into the Body Part and interacts with the Inner Structure. The Lasers 1-N scatter inside the Body Part with a portion of the light being returned to the Photo Detector ring wherein it is detected. The detected light corresponds to the Inner Structure. In this embodiment, Lasers 1-N scattering off the surface of the Body Part do not reach the Photo Detectors on the Photo Detector ring, and therefore, do not interfere with the signal created when the Lasers 1-N interact with the Inner Structure. Accordingly, the power of the Lasers 1-N can be increased substantially to reach deeper Inner Structures without having the surface reflections creating "noise".

In FIGS. 2 to 6 the Photo Detectors are not shown with the electronics attaching them to a system. Such connectivity between the Photo Detectors and the system can be via a wired connection, a wireless connection, an optical connection, or any other transmission technique. Accordingly, a wide array of devices can be envisioned. For example, the Photo Detector array of FIG. 4 can be built into an armrest of a phlebotomy chair. In this case, when a person's arm is placed down on the armrest, the Photo Detectors are in contact with the skin. Alternatively, the photo array of FIG. 4 can be a wireless patch which gets affixed with some type of temporary adhesive to the body part and which wireless communicates the output of the Photo Detectors to the system.

The transillumination laser systems described herein can be utilized as a multispectral system for detecting bruising and erythema (which might indicate developing pressure ulcers). For example, an article in Laser Focus World, having the title "MEDICAL IMAGING: Real-time multispectral imager promises portable-diagnosis," describes a conventional CCD camera system for detection having a masked filter array for receiving images with the following frequencies of light 460, 525, 577 and 650 nm for detection of bruising or 540, 577, 650 and 970 for detection of erythema. However, such a system differs significantly from the transillumination laser system in that the CCD camera receives the light reflected off the skin, and therefore, does not have the same contrast ratio (or signal to noise performance) as transillumination laser system utilizing the same light frequencies for viewing events under the skin. Accordingly, a transillumination laser system utilizing the frequencies, for example 460, 525, 540, 577, 650 and 970 nm can be configured as described in FIGS. 3 to 6 for the detection of both bruising and erythema. The CCD camera system described is further limited in that the number of pixels of the CCD array gets reduced due to the masked filter. Accordingly, the density of the CCD imaging gets divided down by the number of frequencies in the mask. The laser system does not have this limitation in that a complete frame can be taken with each frequency of laser light.

While the laser system of FIG. 2 and the transillumination laser systems of FIGS. 3 to 5 have been herein describe with regard to multispectral laser systems, wherein more than one frequency of light is utilized, the transillumination described herein is applicable to the single frequency detection systems described in the parent applications hereto for the detection of blood vessels within a body.

Closed Loop Projection

Traditional CCD cameras have a large number of pixels that provide a high-resolution image. However, with conventional CCD cameras, each of the pixels has a common exposure time, and the camera lens typically has a single optical aperture setting per picture. Accordingly, it is very difficult to take a very good picture of a very bright item positioned very close to a very dim item. For example, if you were to attempt to take a picture of a seagull next to the sun, if you set the exposure time down (short) and/or the lens aperture opening so small (higher F number) that the sun does not saturate the CCD pixels, you could image the sun but the image of the seagull would be washed out. Conversely, if you set the exposure time long, and the lens aperture opened wide (smaller F number), you could image the bird but the sun would saturate the CCD pixels corresponding to it.

Figure 6:
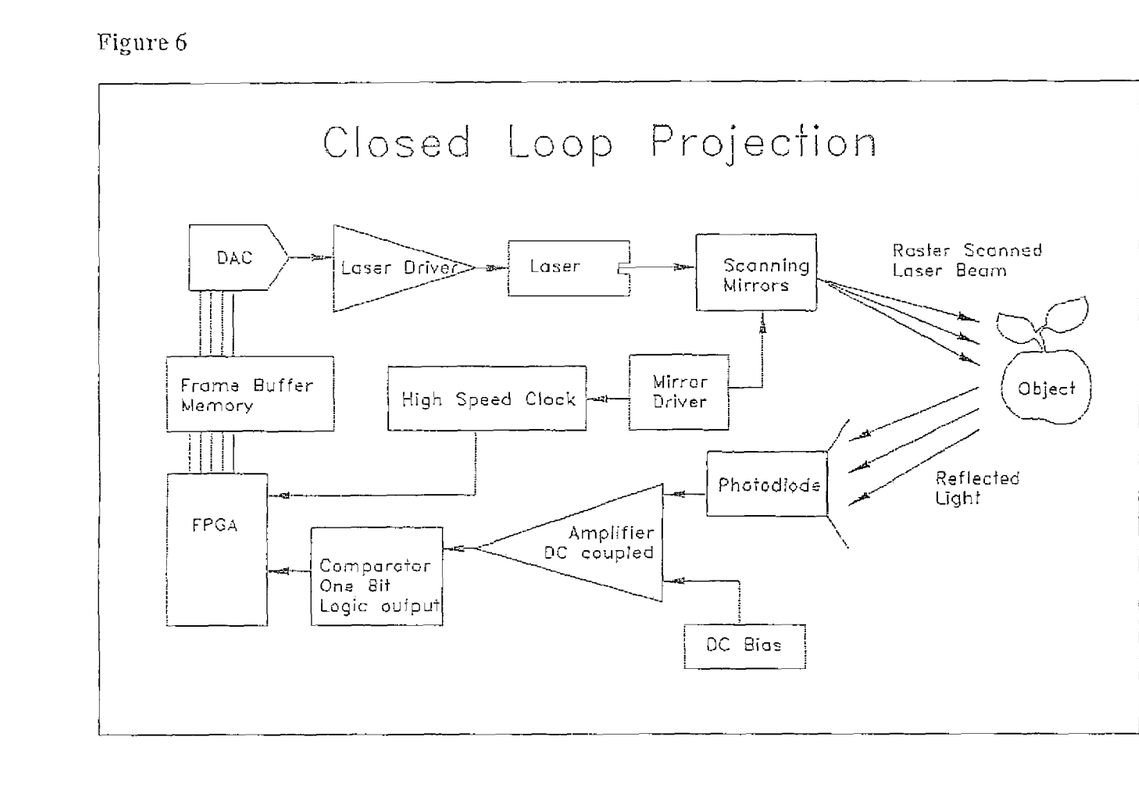
FIG. 6 show s a block diagram of a closed loop projection system capable of capturing images with high dynamic range.

Described in FIG. 6 is a closed loop laser imaging system that is capable of capturing images with very high dynamic range. In the parent application hereto, laser image capture systems are described in which the projected laser light is provided by a raster seamed laser beam. In FIG. 6, the laser, scanning mirrors, photo diodes, mirror drives can all be the same as previously described.

In FIG. 6 the laser beam brightness is controlled by a high speed DAC (digital to analog converter). This DAC is capable of varying the intensity of the laser at a very high rate (hundreds to thousands of times in each horizontal scan). Each segment of a duration corresponding to a desired resolution of the image will be referred hereafter as a pixel. Each pixel of the image has a memory location in the Frame Memory Buffer. Each pixel has a defined location on the object defined by a time slot in the frame.

A Photo Detector (or multiple Photo Detectors or Photo Detector array) receives the reflected light and provides a corresponding voltage to the Amplifier (DC coupled). The output is then provided to the Comparator (One Bit Logic Output) that in turn provides one bit of data. That one bit indicates whether the laser was "too bright" or "too dark" for that pixel. The result is then stored as Pixel brightness information and is updated with every frame. Stored pixel brightness is changed up or down depending on the Photo Detector bit. For maximum light contrast sensitivity, pixel data is always changed by at least one bit every frame. In this manner the closed loop projection image is constantly capturing.

Figure 7:
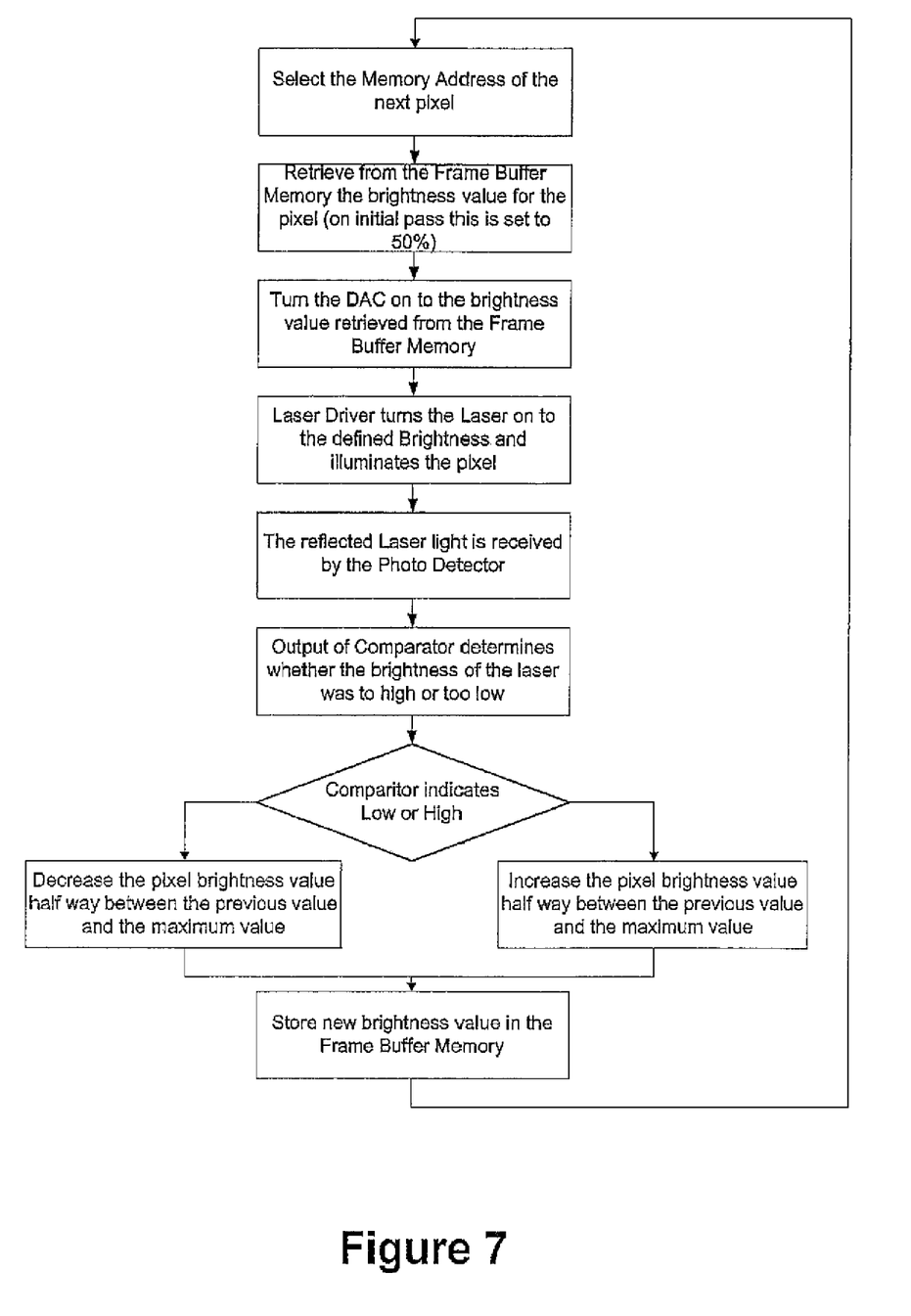
FIG. 7 shows a flow chart illustrating the functioning of the system of FIG. 6.

FIG. 7 is a flow chart illustrating the functioning of the system of FIG. 6.

Depending on the bits of brightness resolution, the system requires multiple frames to fully capture an image. For example, for 8 bits (255 shades), new image capture requires 8 frames. At 60 frames per second, that's 0.13 seconds to capture. After capture, image is maintained and updated with every frame. Since laser brightness (the DAC setting) is adjusted for each pixel, the reflected light for each pixel approaches one value. That value is the midpoint of the analog Photo Detector signal range. This scheme allows the highest contrast sensitivity and highest DC gain in the front end, because the analog signal approaches a flat line. Therefore the dynamic range of the system is not limited by the dynamic range or speed of the Photo Detector amplifier chain.

It is also possible to further increase the dynamic range and speed up the data acquisition of a closed loop laser imaging system by employing a fast, moderate resolution ADC in place of a single Comparator as described above, but still varying the laser power on a pixel-by-pixel basis to ensure nearly-uniform brightness of the resulting image. In this case, the dynamic range of the system would be generally equal to the product of the bit resolutions of the laser driver and the ADC, while the number of frames needed to capture a full-resolution image will be equal to a dividend of the bit resolutions of the laser driver and the ADC.

The time period during the top scan line of the image is reserved for Laser calibration. During calibration, the laser is driven to a defined maximum and then minimum brightness. During minimum brightness, the DC bias on the Photo Detector amplifier is adjusted to compensate for any change in ambient room lighting.

While FIG. 6 describes a system with a single laser, it is possible to implement a multiple laser system utilizing the closed loop projection method. Each frequency of laser can be sequentially cycled for a frame. Alternatively, multiple photo detectors can be filtered; each arranged to receive only one of the specific frequencies of laser light. In this manner, in each frame each frequency of light can concurrently be processed as shown in FIG. 6. For example, red, green and blue lasers can be utilized, wherein each color has a corresponding Frame Buffer Memory. This would function as a color image capture device. As a further example, a multispectral systems can be build, utilizing the frequencies described above for detection of bruising and erythema. Further, any frequencies of laser can be utilized provided that the photo detectors are capable of receiving such frequencies.

Additionally, the information captured at one wavelength may be used to adjust the laser power of different wavelength. Such wavelength cross-coupling may increase accuracy and/or shorten acquisition time of a multispectral closed loop laser imaging system.

The multispectral laser system FIG. 2, the Transillumination Laser System FIGS. 3 to 5 and the Closed Loop Projection system FIG. 6 can be combined together in a single system so that the advantages of each are provided.

Further, the concept described in the parent applications hereto of adding a visible laser as one of the Laser Freq 1-N can be applied to the multispectral laser system FIG. 2, the Transillumination Laser System FIGS. 3 to 5 and the Closed Loop Projection system FIG. 6.

Wherein it is described herein that the object is a Body Part, the multispectral laser system FIG. 2, the Transillumination Laser System FIGS. 3 to 5 and the Closed Loop Projection system FIG. 6 can be utilized on objects other than Body Parts. For example, they can be used on metals for detecting stress fractures, or can be used on plastic parts for detecting imperfections.

System for Evaluating Teeth

Figure 8:
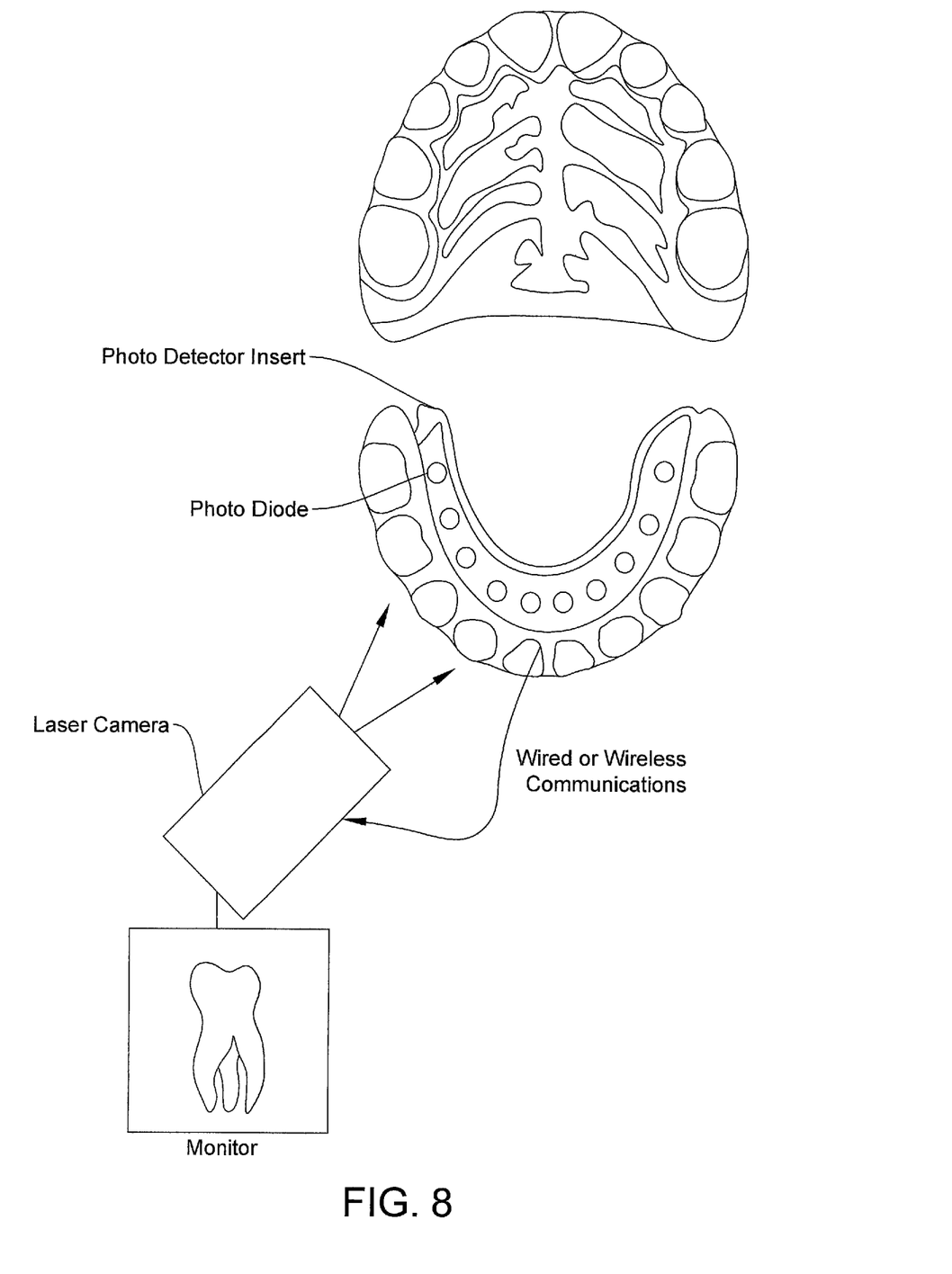
FIG. 8 shows a laser camera system for capturing images of a tooth.

FIG. 8 shows a Laser Camera for capturing images of teeth. The Laser Camera can be designed as previously described in this application and the parent applications. A 1310 nm laser can be utilized as the laser source for imaging. It is known that the frequency of 1310 nm partially passes through teeth. The presence of cavity or other abnormalities will interfere with the reflection of the light. The laser light is transmitted in a raster pattern (or repetitive pattern) towards the teeth. Given that the tooth is relatively small, the laser beam is focused down to a very small spot size by focusing lens within the Laser Camera. The maximum angle of the of transmitted pattern is made relatively small so that the light falls on a single tooth (or a small number of teeth).

The Laser Camera can be configured as a Transillumination Laser Camera, as previously described. A Photo Detector Insert, containing multiple Photo Diodes, can be placed inside the mouth of the patient and pressed against the backside of the teeth. The Photo Detector insert will receive the laser light that is transmitted through the tooth. The Photo Detector Insert can be molded out of a transmissive gummy material so that it can slightly adhere to the backside of the teeth and provides an optical path for the 1310 nm light that scatters within the tooth and passes the light to the Photo Diodes. The light which is received by the Photo Detector Insert is converted to a signal (circuit not shown) which is then communicated (either wired or wirelessly) to the Laser Camera where the results are clocked into an image memory. Once a frame of data is clocked into an image memory it can then be output on a Monitor where the user can view the image of the teeth.

The Laser Camera can be designed as a closed loop imaging system as describe previously in FIGS. 6 and 7. Without the closed loop imaging system, if there are gaps between the teeth, the projected laser will pass through such gaps and saturate the Photo Detector Insert. The very high dynamic range provided by the closed loop imaging system will be beneficial in being able to pick out subtle details, such as cavities and cracks, that are directly next to the very bright spots caused by the gaps in the teeth. The laser power will be able to be substantially increased at specific pixels requiring more illumination, while being reduced requiring a lesser light source (such as the gaps in the teeth).

The Laser Camera can also be a multispectral camera as previously described, wherein the 1310 nm frequency is utilized with other frequency lasers for detecting other characteristics of the teeth.

We claim:

1. A trans-illumination imaging system configured to capture an image of a deep internal feature of an object without noise created by reflections from a surface of the object, and for projecting a high contrast-ratio image of the deep internal feature onto the surface of the object, said trans-illumination imaging system comprising:
   means for transmitting a beam of light comprising at least one infrared wavelength and a visible wavelength;
   means for scanning said beam of light in a first direction and in a second direction, with a first maximum angle between said beam of light at a beginning and an end of said first scan direction, and with a second maximum angle between said beam of light at a beginning and an end of said second scan direction, for scanning said beam of light along a plurality of optical paths in a scan pattern directed upon a first portion of the surface of the object;
   a plurality of photo detectors, each of said photodetectors being spaced apart and at a respective position relative to the surface of the object;
   wherein each of said photo detectors are positioned distally from said means for scanning to receive a contrasted image formed by absorption and reflection of said scanned infrared light by the deep internal feature, without any reflection of said scanned infrared light from said first portion of the surface of the object; and
   wherein each said photo detector is further configured to output a signal of the contrasted image to said means for scanning, for scanning of the contrasted image onto a viewing surface, using said visible wavelength of light.

2. The trans-illumination imaging system according to claim 1, wherein said viewing surface upon which the contrasted image is scanned is the surface of the object.

3. The trans-illumination imaging system according to claim 1, further comprising: means for restricting a field of view of each said photo detector to a respective portion of the surface of the object, each said respective portion of the surface of the object being exclusive of said first portion of the surface directly illuminated by said scanned beam of light.

4. The trans-illumination imaging system according to claim 1, wherein each of said photodetectors are positioned in contact with a respective portion of the surface of the object.

5. The trans-illumination imaging system according to claim 1, wherein said system is configured to use a first power level and a second power level, with said second power level being higher than said first power level, for said second power level to image deeper into the object than said first power level.

6. The trans-illumination imaging system according to claim 1, wherein said plurality of photodetectors are arranged in a grid pattern.

7. The trans-illumination imaging system according to claim 1,
   wherein said infrared wavelength is about 1310 nm;
   wherein said plurality of photodetectors are positioned in a transmissive gummy material configured to releasably adhere to a tooth in a mouth of a patient; and
   wherein said viewing surface is on a monitor.

8. An imaging system configured to capture an image of a deep internal feature of an object without noise created by reflections from a surface of the object, and for projecting a high contrast-ratio image of the deep internal feature onto the surface of the object, said imaging system comprising:
   means for transmitting a beam of light comprising at least one infrared wavelength and a visible wavelength;
   means for scanning said beam of light in a first direction and in a second direction, with a first maximum angle between said beam of light at a beginning and an end of said first scan direction, and with a second maximum angle between said beam of light at a beginning and an end of said second scan direction, for scanning said beam of light along a plurality of optical paths in a scan pattern directed upon a first portion of the surface of the object;
   a plurality of photo detectors, each of said photodetectors being spaced apart at a respective position relative to the surface of the object;
   wherein each of said photo detectors are positioned distally from said means for scanning to receive a contrasted image formed by absorption and reflection of said scanned infrared light by the deep internal feature, without any reflection of said scanned infrared light from said first portion of the surface of the object; and
   wherein each said photo detector is further configured to output a signal of the contrasted image to said means for scanning, for scanning of the contrasted image onto a viewing surface, using said visible wavelength of light.

9. The imaging system according to claim 8, wherein said viewing surface upon which the contrasted image is scanned is the surface of the object.

10. The imaging system according to claim 8, further comprising: means for restricting a field of view of each said photo detector to a respective portion of the surface of the object, each said respective portion of the surface of the object being exclusive of said first portion of the surface directly illuminated by said scanned beam of light.

11. The imaging system according to claim 8, wherein each of said photodetectors are positioned in contact with a respective portion of the surface of the object.

12. The imaging system according to claim 8, wherein said system is configured to use a first power level and a second power level, with said second power level being higher than said first power level, for said second power level to image deeper into the object than said first power level.

13. The imaging system according to claim 8, wherein said plurality of photodetectors are arranged in a grid pattern.

* * * * *